(12) United States Patent
Gong et al.

(10) Patent No.: US 9,724,729 B2
(45) Date of Patent: Aug. 8, 2017

(54) METHOD OF MODIFYING A COATING ON A MEDICAL DEVICE

(75) Inventors: Victoria M. Gong, Sunnyvale, CA (US); John Stankus, Campbell, CA (US); Stephen D. Pacetti, San Jose, CA (US); Anthony S. Andreacchi, San Jose, CA (US); Benny Serna, Gilroy, CA (US); Binh Nguyen, Newark, CA (US)

(73) Assignee: ABBOTT LABORATORIES, Santa Clara, CA (US)

( * ) Notice: Subject to any disclaimer, the term of this patent is extended or adjusted under 35 U.S.C. 154(b) by 728 days.

(21) Appl. No.: 12/976,279

(22) Filed: Dec. 22, 2010

(65) Prior Publication Data
US 2012/0165922 A1 Jun. 28, 2012

(51) Int. Cl.
*B05D 3/00* (2006.01)
*A61F 2/82* (2013.01)
*B05D 3/10* (2006.01)
*A61L 27/34* (2006.01)
*A61L 27/50* (2006.01)

(52) U.S. Cl.
CPC ............. *B05D 3/107* (2013.01); *A61L 27/34* (2013.01); *A61L 27/50* (2013.01); *A61L 2400/18* (2013.01)

(58) Field of Classification Search
CPC .................................... B05D 3/00; A61F 2/82
USPC .......................................................... 427/2.1
See application file for complete search history.

(56) References Cited

U.S. PATENT DOCUMENTS

| 5,464,650 | A | 11/1995 | Berg et al. |
| 5,591,227 | A | 1/1997 | Dinh et al. |
| 5,649,977 | A | 7/1997 | Campbell |
| 7,335,227 | B2 | 2/2008 | Jalisi |
| 7,378,105 | B2 | 5/2008 | Burke et al. |
| 7,445,792 | B2 | 11/2008 | Toner et al. |
| 2004/0180039 | A1* | 9/2004 | Toner et al. ............... 424/93.2 |
| 2005/0226991 | A1* | 10/2005 | Hossainy .......... A61M 25/1029 427/2.1 |
| 2006/0184112 | A1* | 8/2006 | Horn ................... A61M 25/104 604/103.08 |
| 2009/0226502 | A1* | 9/2009 | Chen ..................... A61L 29/085 424/423 |
| 2010/0233236 | A1* | 9/2010 | Zhao .................... A61K 31/337 424/423 |
| 2010/0266656 | A1* | 10/2010 | Johnson ................ A61L 29/06 424/423 |
| 2010/0286608 | A1* | 11/2010 | Tittelbach .............. A61L 29/16 604/103.01 |

(Continued)

OTHER PUBLICATIONS

Anthanmatten et al., Controlling Surface Roughness in Vapor Deposited Poly(amic acid) Films by Solvent-Vapor Exposure, Nov. 4, 2003, Langmuir Journal.*

(Continued)

*Primary Examiner* — Dah-Wei D Yuan
*Assistant Examiner* — Hai Yan Zhang
(74) *Attorney, Agent, or Firm* — Baker Botts L.L.P.

(57) ABSTRACT

Method of modifying the coating of a surface of a medical device by applying a coating to the surface of the medical device, exposing the medical device to an environmental condition that alters the coating morphology, and drying the coating on the medical device. The disclosed subject matter also provides a coated medical device whose one or more surfaces have been modified by this method.

36 Claims, 8 Drawing Sheets

(56) References Cited

U.S. PATENT DOCUMENTS

2011/0008260 A1* 1/2011 Flanagan .............. A61L 29/16
424/9.3
2012/0316496 A1* 12/2012 Hoffmann ............ A61L 29/085
604/103.02

OTHER PUBLICATIONS

Cyclohexane Solvent Properties, CAS 101-82-7.*
Unverdoben, Martin, "The Paclitaxel-Eluting PTCA-Balloon Catheter in Coronary Artery Disease PEPCAD I-SVD PEPCAD II-ISR," Clinical Research Institute, Center for Cardiovascular Diseases, 2005-2006, Rotenberg, Germany.

* cited by examiner

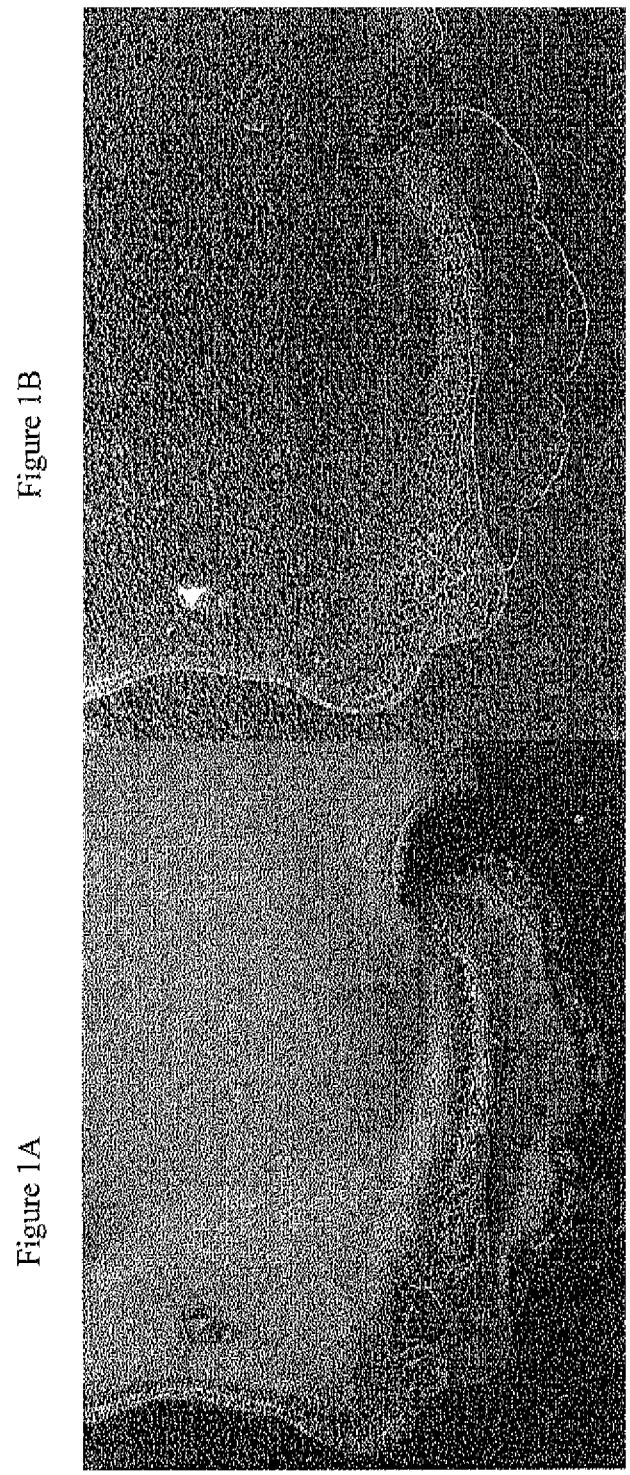

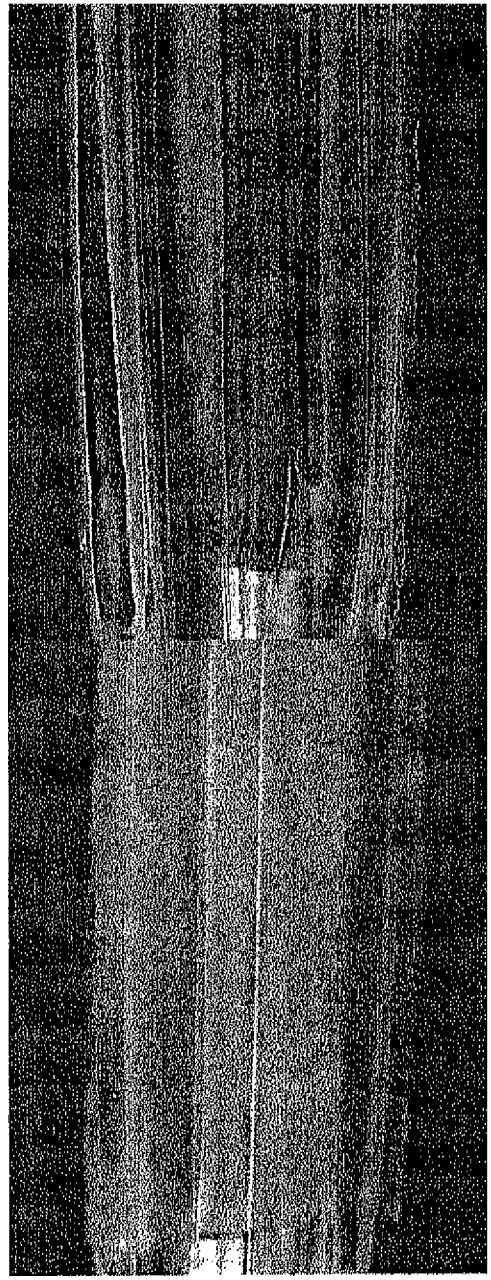

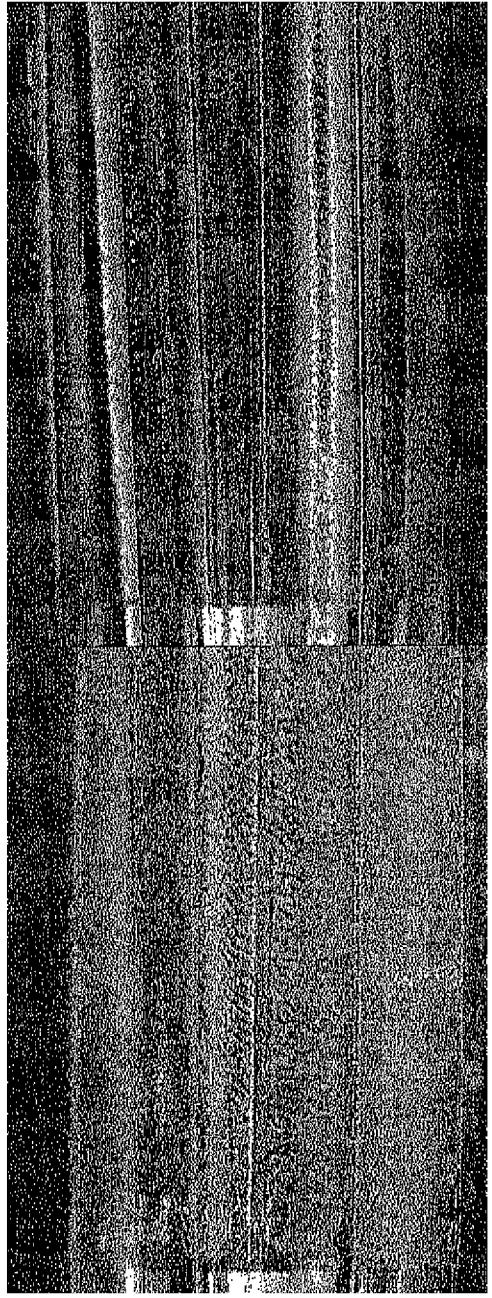

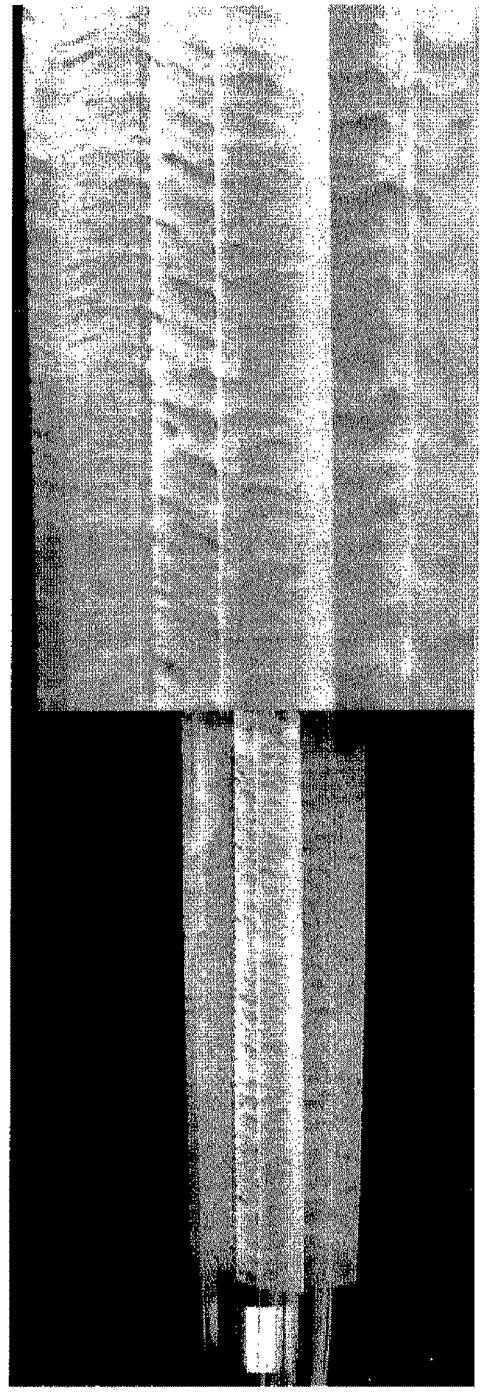

METHOD OF MODIFYING A COATING ON A MEDICAL DEVICE

FIELD OF THE DISCLOSED SUBJECT MATTER

The presently disclosed subject matter relates to a method of modifying a coating on a medical device. More particularly, the presently disclosed subject matter relates to a method of using vapor treatment to modify the coating morphology of a coated medical device to increase uniformity and decrease coating defects. The disclosed subject matter also relates to a coated medical device with at least one surface modified by this method.

DESCRIPTION OF RELATED SUBJECT MATTER

Atherosclerosis is a syndrome affecting arterial blood vessels. It is characterized by a chronic inflammatory response in the walls of arteries, which is in large part due to the accumulation of lipid, macrophages, foam cells and the formation of plaque in the arterial wall. Atherosclerosis is commonly referred to as hardening of the arteries, although the pathophysiology of the disease manifests itself with several different types of lesions ranging from fibrotic to lipid laden to calcific. Angioplasty is a vascular interventional technique involving mechanically widening an obstructed blood vessel, typically caused by atherosclerosis.

During angioplasty, a catheter having a folded balloon is inserted into the vasculature of the patient and is passed to the narrowed location of the blood vessel at which point the balloon is inflated to the desired size by fluid pressure. Percutaneous coronary intervention (PCI), commonly known as coronary angioplasty, is a therapeutic procedure to treat the stenotic regions in the coronary arteries of the heart, often found in coronary heart disease. In contrast, peripheral angioplasty, commonly known as percutaneous transluminal angioplasty (PTA), generally refers to the use of mechanical widening of blood vessels other than the coronary arteries. PTA is most commonly used to treat narrowing of the leg arteries, especially, the iliac, external iliac, superficial femoral and popliteal arteries. PTA can also treat narrowing of carotid and renal arteries, veins, and other blood vessels.

Although the blood vessel is often successfully widened by angioplasty, sometimes the treated region of the blood vessel undergoes vasospasm, or abrupt closure after balloon inflation or dilatation, causing the blood vessel to collapse after the balloon is deflated or shortly thereafter. One solution to such collapse is stenting the blood vessel to prevent collapse. Dissection, or perforation, of the blood vessel is another complication of angioplasty that can be improved by stenting. A stent is a device, typically a metal tube or scaffold that is inserted into the blood vessel after, or concurrently with angioplasty, to hold the blood vessel open.

While the advent of stents eliminated many of the complications of abrupt vessel closure after angioplasty procedures, within about six months of stenting a re-narrowing of the blood vessel can form, a condition known as restenosis. Restenosis was discovered to be a response to the injury of the angioplasty procedure and is characterized by a growth of smooth muscle cells and extracellular matrix—analogous to a scar forming over an injury. To address this condition, drug eluting stents were developed to reduce the reoccurrence of blood vessel narrowing after stent implantation. A drug eluting stent is a stent that has been coated with a drug, often in a polymeric carrier, that is known to interfere with the process of re-narrowing of the blood vessel (restenosis). Examples of various known drug eluting stents are disclosed in U.S. Pat. Nos. 5,649,977; 5,464,650; 5,591,227, 7,378,105; 7,445,792; 7,335,227, all of which are hereby incorporated by reference in their entirety. However, drug eluting stents are not without limitations.

Drug coated balloons are believed to be a viable alternative to drug eluting stents in the treatment of atherosclerotic lesions. In a study which evaluated restenosis, and the rate of major adverse cardiac events such as heart attack, bypass, repeat stenosis, or death in patients treated with drug coated balloons and drug eluting stents, the patients treated with drug coated balloons experienced only 3.7% restenosis and 4.8% MACE (material adverse coronary events) as compared to patients treated with drug eluting stents, in which restenosis was 20.8 percent and 22.0 percent MACE rate. (See, PEPCAD II study, Rotenburg, Germany).

A drug coated balloon is a unique drug-device combination product. In addition to performing a dilatation function, the balloon delivers a therapeutic level of drug to the vascular tissue during an inflation that can last from only a few seconds to several minutes. This rapid transfer of drug requires a coating capable of releasing a suitable amount of drug during the balloon inflation. There are a variety of potential mechanisms of drug transfer for a drug coated balloon, including: transfer of coating to the vessel wall with subsequent diffusion of drug into tissue; insertion of coating into tissues or fissures in the vessel wall produced by the dilatation; pressing the coating against the vessel wall, the drug dissolving into a thin liquid film to create a drug saturated boundary layer, and this dissolved drug diffusing into the tissue; and drug dissolving the entire time the balloon is near, or expanded against, the vessel wall and this dissolved drug diffusing into the tissue.

However, drug coated balloons present certain unique challenges. For example, the drug carried by the balloon needs to remain on the balloon during delivery to the lesion site, and released from the balloon surface to the blood vessel wall when the balloon is expanded inside the blood vessel. For coronary procedures, the balloon is typically inflated for less than one minute, typically about thirty seconds. The balloon inflation time can be longer for a peripheral procedure, however typically even for peripheral procedures the balloon is expanded for less than five minutes. Due to the short duration of contact between the drug coated balloon surface and the blood vessel wall, the balloon coating must exhibit efficient therapeutic agent transfer and/or efficient drug release during inflation. Thus, there are challenges specific to drug delivery via a drug coated or drug eluting balloon that are not present with a drug eluting stent. Furthermore, volatile solvents are often used for coating formulations, since the rate of evaporation is rapid. This allows minimal flow as the coating solidifies onto the surface of the medical device. However, these rapid evaporation rates can alter the surface characteristics of the coatings and system equilibrium is not always attained prior to solidification. As a result, surfaces can exhibit nonuniformities such as entrapped air-bubbles, ribbing or streaking, dimpling, wrinkles, peeling, and fibers. More common observations are crack propagation, poor coating adhesion, an increase in coating porosity and pore size, coating separation from the balloon surface, nonuniform thicknesses of coatings, and uncontrolled crystal growth. These defects can negatively impact product performance.

Mechanical manipulations of a drug coated balloon into a folded state for deliverability and trackability purposes have also been problematic since such folding can result in non-uniform or brittle coatings. Moreover, any mechanical post-coating attempts to adjust imperfections, such as vacuuming or drying surface imperfections, can also change the coating composition and drug dosage undesirably. Furthermore, contacting a solidified coating with a liquid solvent can redistribute or extract drug or allow migration of the coating solids under the influence of gravity.

Thus, there remains a need for an efficient and economic method of modifying the coating morphology of a coated medical device to increase uniformity and decrease coating defects. The disclosed subject matter addresses this need by exposing the medical device to an environmental condition sufficient to alter the coating morphology.

SUMMARY OF THE DISCLOSED SUBJECT MATTER

The purpose and advantages of the disclosed subject matter will be set forth in and apparent from the description that follows, as well as will be learned by practice of the disclosed subject matter. Additional advantages of the disclosed subject matter will be realized and attained by the methods and medical device particularly pointed out in the written description and claims hereof, as well as from the appended drawings.

To achieve these and other advantages and in accordance with the purpose of the disclosed subject matter, as embodied and broadly described, the disclosed subject matter includes a method of modifying the coating on a coated medical device in order to increase coating uniformity.

In accordance with one aspect of the disclosed subject matter, a method of modifying a coating is provided. The method includes applying a coating to at least a surface of a medical device wherein the coating has an initial coating morphology, exposing the coating to a specific environmental condition, and drying the coating on the coated medical device. The method of modifying the coating of a coated medical device can further include curing the coating on the surface of the medical device prior to exposing the medical device to the environmental condition. Additionally or alternatively, the coating can be cured after exposing the medical device to the environmental condition.

In one embodiment, curing includes initially drying the coating. Initial drying of the coating on the medical device can include removing residual solvent from the coating. Initial drying can occur in a closed or semi-enclosed system, simultaneously with exposure to the environmental condition, or by applying directed vapor in line. In one embodiment, the directed vapor applied in a line is carried out via a nozzle located between about 1 mm and about 200 mm from the medical device. The directed vapor is applied at a pressure between about 10 torr and about 1520 torr.

The coating can be applied by spraying, syringe coating, spin coating, vapor deposition, roll coating, micro-droplet coating, drip coating, dip coating, electrospinning, electrostatic coating, direct vapor application or a combination thereof. The coating can include a polymeric coating, elastomeric coating, hydrophilic coating, hydrophobic coating, drug coating, drug excipient coating, biologic agent coating, protein coating, silicone coating, radiopaque coating, or a combination thereof.

In one embodiment, the coating includes a therapeutic agent. The therapeutic agent can include an anti-proliferative agent, anti-inflammatory agent, anti-thrombotic agent, thrombolytic agent, anticoagulant agent, antiplatelet agent, anti-metabolite agent, smooth muscle cell migration inhibiting agent, anti-smooth muscle cell proliferation agent, reendothelialization agent, plaque deposition inhibiting agent, restenosis-limiting agent, or a combination thereof. More particularly, the coating can include everolimus, zotarolimus, rapamycin, biolimus, myolimus, novolimus, deforolimus, temsirolimus, paclitaxel, protaxel, analogs and derivatives thereof, or a combination thereof.

The medical device can be a balloon catheter, stent, stent graft, surgical mesh, vascular graft, venous graft, aortic graft, guide wire, vascular filter, cerebral aneurysm filler coil, intraluminal paving system, suture, staple, anastomosis device, vertebral disk, bone pin, suture anchor, hemostatic barrier, clamp, screw, plate, clip, sling, vascular implant, cardiac defibrillator lead, heart valve, mitral clip, tissue adhesive or sealant, tissue scaffold, myocardial plug, pacemaker lead, embolic coil, dressing, bone substitute, intraluminal device, vascular support and other known biocompatible devices.

In accordance with another aspect of the disclosed invention, exposing the medical device to the environmental condition includes exposing the medical device to a vapor in a gaseous or vapor state. In one embodiment, the vapor has a vapor pressure between about 0.5 torr and about 420 torr at 20° C. In certain embodiments, the vapor can be volatile. In one embodiment, the volatile vapor has a boiling point at ambient pressure in the range of about 25° C. to about 185° C. The volatile vapor can include acetone, ethanol, linear alcohols, methane, ethane, heptane, hexane, methyl isobutyl ketone, methyl ethyl ketone, dimethylsulfoxide, ethyl acetate, heptane, pentane, 2-propanol, N-methylpyrrolidone, dichloromethane, chloroform, blends thereof, and combinations thereof. The vapor can include a solvent used when exposing the coating to the surface of the medical device. In another embodiment, the vapor is aqueous.

In one embodiment, the coating has a glass transition temperature and exposing the medical device to the environmental condition includes maintaining a temperature above the glass transition temperature of the coating on the medical device. In another embodiment, exposing the medical device to the environmental condition causes the glass transition temperature of the coating to drop so that it is below the temperature of the environmental condition.

In certain embodiments, exposing the medical device to the environmental condition comprises exposing the device to ambient temperature. In accordance with another aspect of the disclosed subject matter, exposing the medical device to the environmental condition includes maintaining a temperature between about 20° C. to about 110° C. In one embodiment, the temperature is maintained between about 40° C. to about 70° C. In another embodiment, the temperature is maintained between about 40° C. to about 50° C. In one embodiment, exposing the medical device to the environmental condition includes maintaining a pressure that ranges from about 10 torr to about 1520 torr.

In another embodiment, the medical device is kept stationary while exposing the medical device to the environmental condition. Alternatively, or additionally, the medical device can be rotated while exposing the medical device to the environmental condition. The medical device can be rotated manually or automatically via a rotating motor at set speeds greater than zero RPM. The medical device can be rotated at set speeds between about 5 RPM and about 700 RPM. Alternatively, or additionally, the medical device can be attached to a stage and the stage can be linearly translated at a speed between about 0.1 mm/sec to about 5 mm/sec.

In accordance with another aspect of the disclosed subject matter, exposing the medical device to the environmental condition includes placing at least a portion of the medical device in a closed or semi-enclosed system. The closed system can be an enclosed chamber.

In one embodiment, exposing the medical device to the environmental condition comprises applying directed solvent vapor in line. The directed vapor in a line can be applied via a nozzle located between about 1 mm and about 200 mm from the medical device. The directed vapor can be applied at a pressure between about 10 torr and about 1520 torr.

It is to be understood that both the foregoing and the following descriptions are exemplary and are intended to provide further explanation of the disclosed subject matter claimed to a person of ordinary skill in the art. The accompanying drawings are included to illustrate various embodiments of the disclosed subject matter to provide a further understanding of the disclosed subject matter. The exemplified embodiments of the disclosed subject matter are not intended to limit the scope of the claims.

BRIEF DESCRIPTION OF THE DRAWINGS

FIGS. 1A and 1B are optical micrographs at 30× of a glass slide coating, wherein FIG. 1A shows the glass slide coating prior to acetone vapor exposure and FIG. 1B shows the same slide after exposure as described in Example 1.

FIGS. 2A and 2B are optical micrographs at 150× of a glass slide coating, wherein FIG. 2A shows the glass slide coating prior to acetone vapor exposure and FIG. 2B shows the same slide after exposure as described in Example 1.

FIGS. 3A and 3B are optical micrographs at 200× of a glass slide coating, wherein FIG. 3A shows the glass slide coating prior to acetone vapor exposure and FIG. 3B shows the same slide after acetone vapor exposure as described in Example 1.

FIGS. 4A and 4B are optical micrographs at 40× of a drug coated balloon with a coating of 88 µg/cm$^2$, wherein FIG. 4A shows the drug coated balloon prior to acetone vapor exposure and FIG. 4B shows the drug coated balloon after exposure as described in Example 2.

FIGS. 5A and 5B are optical micrographs at 50× of a drug coated balloon with a coating of 400 µg/cm$^2$, wherein FIG. 5A shows the drug coated balloon prior to acetone vapor exposure and FIG. 5B shows the drug coated balloon after exposure as described in Example 2.

FIGS. 7 and 8 are optical micrograph images of a drug coated balloon, wherein FIGS. 7A and 8A are at 50×, FIGS. 7B and 8B are at 100×, FIGS. 7C and 8C are at 200×, and FIGS. 7D and 8D are at 400×. FIG. 7 depicts the drug coated balloon prior to humidity exposure and FIG. 8 depicts the same balloon after exposure as described in Example 5.

DETAILED DESCRIPTION

Figures 2A, 2B:

Reference will now be made in detail to the preferred embodiments of the disclosed subject matter. The method and corresponding steps of the disclosed subject matter will be described in conjunction with the detailed description of the system.

In accordance with the disclosed subject matter, a method is provided for modifying the coating morphology of a surface of a medical device. Particularly, the disclosed subject matter provides a method including applying a coating to a surface of a medical device wherein the coating has an initial coating morphology, exposing the medical device to an environmental condition sufficient to alter the coating morphology, and drying the coating.

The disclosed subject matter also includes a medical device whose coating morphology is modified by applying a coating to a surface of a medical device, exposing the medical device to an environmental condition sufficient to alter the coating morphology, and drying the coating.

Definitions

The terms used in this specification generally have their ordinary meanings in the art, within the context of this invention and in the specific context where each term is used. Certain terms are defined below to provide additional guidance in describing the compositions and methods of the invention and how to make and use them.

The phrase "in line" as used herein refers to application of a directed stream of liquid or vapor to a device during the manufacturing process. It may occur simultaneously, or in sequence, with the coating or drying process. The stream, device, or both are moved so that the trajectory of the stream moves horizontally, vertically, or diagonally in a straight line.

The term "crazing" as used herein refers to cracks and fractures or the like in a coating.

The term "vapor" as used herein refers to one or more chemicals or mixtures thereof in a gas or vapor phase.

The term "closed system" as used herein refers to any sealed or fully enclosed apparatus, chamber, vessel, device, or enclosure that serves as a complete barrier between the environment within the apparatus, chamber, vessel, device, or enclosure and the ambient environment.

The term "semi-closed system" as used herein refers to any partially sealed or partially enclosed apparatus, chamber, vessel, device, or enclosure that serves as a barrier between the environment within the apparatus, chamber, vessel, device, or enclosure and the ambient environment.

The term "porosity" as used herein refers to porousness, or more particularly the number and size of pores, striations, and other interstices within a coating. When a first region is said to have a lower porosity than a second region, it is meant that the first region has fewer and/or smaller pores, striations, or interstices within the coating.

The term "crystallinity" as used herein refers to the measure of regularity with which molecules of the coating or a component thereof are aligned into planes and/or lattices. When a first region is said to have a lower crystallinity than a second region, it is meant that there are fewer planes, that the planes are smaller, and/or that the first region is more amorphous than the second region.

As used in the specification and the appended claims, the singular forms "a," "an" and "the" include plural referents unless the context clearly dictates otherwise. Thus, for example, reference to "a compound" includes mixtures of compounds.

The term "about" or "approximately" means within an acceptable error range for the particular value as determined by one of ordinary skill in the art, which will depend in part on how the value is measured or determined, i.e., the limitations of the measurement system. The error of a measured value may be described by the standard deviation (SD) with an acceptable value lying in the range of ±2SD. For instance, the term "about" as used herein refers to a pressure error of ±5 PSI or ±10 torr, RPM error of ±5 RPM; mm/sec error of ±0.1 mm/sec; and mm error off 2 mm.

Environmental Conditions

In accordance with the disclosed subject matter, exposing the medical device to an environmental condition comprises exposing the medical device to a vapor in a gaseous or vapor state. In one embodiment, the vapor has a vapor pressure between about 0.5 torr and about 420 torr at 20° C. Exposure can occur passively or actively, for example via active convection or blowing of the vapor on the coating. In accordance with another aspect of the disclosed subject matter, the vapor is volatile. For example, the volatile vapor has a boiling point at ambient pressure in the range of about 25° C. to about 185° C. In another embodiment, the vapor is aqueous. In yet another non-limiting embodiment, the vapor comprises a solvent used when exposing the coating to the surface of the medical device.

Examples of suitable vapors include, but are not limited to, water, acetone, methanol, ethanol, 2-propanol, 1-propanol, linear alcohols, methane, ethane, propane, butane, pentane hexane, cyclohexane, heptane, methyl iso-butyl ketone, methyl ethyl ketone, dimethylsulfoxide, dimethylacetamide, dimethylformamide, formamide, methyl acetate, ethyl acetate, propyl acetate, isopropyl acetate, n-butyl acetate, dimethyl ether, diethyl ether, dipropyl ether, N-methylpyrrolidone, dichloromethane, chloroform, difluoromethane, fluoroform, freons, benzene, toluene, xylene, blends thereof, and combinations thereof. Not all vapors will be compatible with all coatings or components thereof. Similarly, not all vapors will be compatible with the compositions and materials of all medical devices or surfaces of medical devices. The preferred vapor can depend on a number of variables depending on the compositions of the coatings and the medical device surfaces. The vapor should be maintained to be above the glass transition temperature of the coating, one or more coating excipients, or one or more coating ingredients. In another non-limiting embodiment, exposing the medical device to the environmental condition causes the glass transition temperature of the coating to drop below the temperature of the environmental condition. In one embodiment, the temperature can be maintained between about 20° C. to about 110° C., preferably between about 40° C. to about 70° C., and more preferably between about 40° C. to about 50° C.

Alternatively or additionally, exposing the medical device to an environmental condition can involve maintaining a pressure. For purposes of illustration and not limitation, the pressure can be between about 10 torr and 1520 torr. A more preferred range would be 50 torr to 760 torr. High vacuum lower than 10 torr would not be expected to produce much of an effect in processes where the medical device is being exposed to vapor. Pressures above ambient (760 torr) can represent a pure solvent vapor while pressures above ambient require pressure vessel equipment or very high local flow rates. The acceptable pressure range would depend on the medical device material to which inflation pressure is being applied.

The medical device can be kept stationary while exposing the medical device to an environmental condition. Alternatively, the medical device can be rotated while it is exposed to the environmental condition. Rotation of the medical device can advantageously provide for homogenous treatment of the coating around the entire coating surface. Rotation can be applied manually or automatically via a rotating motor at set speeds greater than zero rotations per minute (RPM). In one embodiment, the medical device is rotated at set speeds between about 5 RPM and about 700 RPM. Additionally or alternatively, the medical device is attached to a stage and the stage is linearly translated at a speed between about 0.1 min/sec to about 5 mm/sec.

In one embodiment, exposing the medical device to the environmental condition includes placing at least a portion of the medical device in a closed or semi-enclosed system. For example, the closed system can be an enclosed chamber.

In another non-limiting embodiment, exposing the medical device to the environmental condition comprises applying directed solvent vapor in line. In one embodiment, applying directed solvent vapor in line occurs via a nozzle located between about 1 mm and about 200 mm from the medical device. In a preferred embodiment, the directed vapor is at a pressure between about 10 torr and about 1520 torr.

Coating Morphology Modifications

In one aspect of the presently disclosed subject matter, exposing the medical device to the environmental condition can cause internal transformation within the coating without the coating entering a liquid state. Preventing the coating from entering into a liquid state enables the coating to maintain defined edges. Such defined edges are advantageous when it is desirable to prevent coating from flowing from one area of the medical device to another area of the medical device, such as in a drug coated balloon where the working length is controlled and coating flow to the tapered ends is undesirable.

Alternatively or additionally, exposing the medical device to the environmental condition can cause the coating to have reduced crystallinity and become amorphous or semi-amorphous. Alternatively or additionally, exposing the medical device to the environmental condition causes the coating to flow such that the morphology of the coating is altered. The exposure can occur for any length of time sufficient to allow internal transformation within the coating, including but not limited to the coating becoming amorphous, semi-amorphous, or beginning to flow. This is advantageous as it can result in annealing cracks or fractures and thus increasing coating uniformity. In one non-limiting embodiment, the coated medical device is exposed to the environmental condition for a length of time between about 5 minutes and about 18 hours. In another non-limiting embodiment, the coated medical device is exposed to the environmental condition for a length of time between about 5 minutes and about 7 hours. For manufacturing throughput, short exposure times of 30 minutes or less are desired. Factors which will affect the kinetics of the coating modification by the environmental condition include the glass transition temperature of the coating, the solvency of the any solvent vapor used for the coating components, the temperature, and the humidity. Other factors include the volume of the environmental container, the volume of the solvent, the exposed surface area within the container, and the size and quantity of exposed devices.

Further in accordance with the presently disclosed subject matter, a number of advantages can be achieved. By way of illustration and not limitation, the currently disclosed method can reduce frictional force between the coating surface and a protective sheath as compared to a similar medical device having a coating with an unaltered coating morphology. The currently disclosed method can also alter a coating so that the coating has less crazing, or fewer cracks and fractures in the coating as compared to a similar medical device having a coating with an unaltered coating morphology. Another aspect of the presently disclosed subject matter is that it can reduce the porosity of the coating as compared to a similar medical device having a coating with an unmodified coating morphology.

Medical Devices

The methods presented herein can be used for modifying one or more coatings on a medical device. The disclosed subject matter is particularly suited for modifying the morphology of the coating on a catheter, more particularly a drug coated balloon. While the disclosed subject matter references a drug coated balloon, it is to be understood that the methods disclosed herein can also be employed to apply to any medical device with any type of coating.

A wide variety of medical devices are known and suitable for use in accordance with the disclosed subject matter. For example, the medical device can be a balloon catheter made from nylon-12, nylon-6, nylon-6,6, nylon copolymers, Pebax, polyethylene terephthalate, Hytrel, polyester, nylon blends, polyurethane, polyethylene, ethylene vinyl acetate, polyimides, polyamides, polyether urethanes, polysilicone urethanes, and polycarbonate urethanes. Other examples include, but are not limited to, a stent, stent graft, surgical mesh, vascular graft, venous graft, aortic graft, guide wire, vascular filter, cerebral aneurysm filler coil, intraluminal paving system, suture, staple, anastomosis device, vertebral disk, bone pin, suture anchor, hemostatic barrier, clamp, screw, plate, clip, sling, vascular implant, cardiac defibrillator lead, heart valve, mitral clip, tissue adhesive or sealant, tissue scaffold, myocardial plug, pacemaker lead, embolic coil, dressing, bone substitute, intraluminal device, vascular support and other known biocompatible device.

In accordance with one aspect of the disclosed subject matter, the coating can be cured on the surface of the medical device prior to exposing the medical device to the environmental condition. Alternatively or in addition, the coating can be cured on the surface of the medical device after exposing the medical device to the environmental condition. By way of illustration and not limitation, curing the coating can include initial drying of the coating on the medical device. For example, the coating can be dried in closed or semi-closed system, simultaneously with exposure to the environmental condition, or by applying directed vapor in line. In line application drying is characterized by simultaneous or "almost simultaneous" drying with a nozzle or source of air/nitrogen or gaseous mixture at either a high or ambient temperature. In line application drying can occur simultaneously, or in sequence, with the coating or drying process.

In one embodiment, applying directed solvent vapor in line occurs via a nozzle located between about 1 mm and about 200 mm from the medical device. In a preferred embodiment, the directed vapor is at a pressure between about 10 torr and about 1520 torr. Drying the coating can be employed to remove residual solvent from the coating.

In accordance with another aspect, a coating can be applied to the surface of a medical device by any technique or techniques known in the art. Some examples include, but are not limited to, spraying, syringe coating, direct fluid application, spin coating, vapor deposition, roll coating, micro-droplet coating, drip coating, dip coating, electrospinning, electrostatic coating, direct vapor application or a combination thereof.

A wide variety of coatings are suitable for use with the presently disclosed subject matter. For illustration and not limitation, the coating can be a polymeric coating, elastomeric coating, hydrophilic coating, hydrophobic coating, drug coating, drug excipient coating, biologic agent coating, silicone coating, radiopaque coating, or a combination thereof. In one non-limiting embodiment, the coating comprises a therapeutic agent. The therapeutic agent can be, but is not limited to, an anti-proliferative agent, a pro-proliferative agent, anti-inflammatory agent, anti-thrombotic agent, thrombolytic agent, anticoagulant agent, antiplatelet agent, anti-metabolite agent, anti-neoplastic agent, anti-mitotic agent, anti-fibrin agent, cytostatic agent, cytoprotective agent, ACE inhibiting agent, cardioprotective agent, antibiotic agent, anti-allergic agent, antioxidant agent, smooth muscle cell migration inhibiting agent, anti-smooth muscle cell proliferation agent, reendothelialization agent, plaque deposition inhibiting agent, restenosis-limiting agent, or a combination thereof. The term "cytostatic" as used herein means a drug that mitigates cell proliferation but allows cell migration. These cytostatic drugs, include for the purpose of illustration and without limitation, macrolide antibiotics, rapamycin, everolimus, zotarolimus, biolimus A9, deforolimus, AP23572, myolimus, novolimus, tacrolimus, temsirolimus, pimecrolimus, structural derivatives and functional analogues of rapamycin, structural derivatives and functional analogues of everolimus, structural derivatives and functional analogues of zotarolimus and any macrolide immunosuppressive drugs. The term "antiproliferative" as used herein means a drug used to inhibit cell growth, such as chemotherapeutic drugs. Some non-limiting examples of antiproliferative drugs include taxanes, paclitaxel, and protaxel.

Examples of anti-inflammatory drugs include both steroidal and non-steroidal (NSAID) anti-inflammatories such as, without limitation, clobetasol, alclofenac, alclometasone dipropionate, algestone acetonide, alpha amylase, amcinafal, amcinafide, amfenac sodium, amiprilose hydrochloride, anakinra, anirolac, anitrazafen, apazone, balsalazide disodium, bendazac, benoxaprofen, benzydamine hydrochloride, bromelains, broperamole, budesonide, carprofen, cicloprofen, cintazone, cliprofen, clobetasol propionate, clobetasone butyrate, clopirac, cloticasone propionate, cormethasone acetate, cortodoxone, deflazacort, desonide, desoximetasone, dexamethasone, dexamethasone dipropionate, dexamethasone acetate, dexmethasone phosphate, momentasone, cortisone, cortisone acetate, hydrocortisone, prednisone, prednisone acetate, betamethasone, betamethasone acetate, diclofenac potassium, diclofenac sodium, diflorasone diacetate, diflumidone sodium, diflunisal, difluprednate, diftalone, dimethyl sulfoxide, drocinonide, endrysone, enlimomab, enolicam sodium, epirizole, etodolac, etofenamate, felbinac, fenamole, fenbufen, fenclofenac, fenclorac, fendosal, fenpipalone, fentiazac, flazalone, fluazacort, flufenamic acid, flumizole, flunisolide acetate, flunixin, flunixin meglumine, fluocortin butyl, fluorometholone acetate, fluquazone, flurbiprofen, fluretofen, fluticasone propionate, furaprofen, furobufen, halcinonide, halobetasol propionate, halopredone acetate, ibufenac, ibuprofen, ibuprofen aluminum, ibuprofen piconol, ilonidap, indomethacin, indomethacin sodium, indoprofen, indoxole, intrazole, isoflupredone acetate, isoxepac, isoxicam, ketoprofen, lofemizole hydrochloride, lomoxicam, loteprednol etabonate, meclofenamate sodium, meclofenamic acid, meclorisone dibutyrate, mefenamic acid, mesalamine, meseclazone, methylprednisolone suleptanate, momiflumate, nabumetone, naproxen, naproxen sodium, naproxol, nimazone, olsalazine sodium, orgotein, orpanoxin, oxaprozin, oxyphenbutazone, paranyline hydrochloride, pentosan polysulfate sodium, phenbutazone sodium glycerate, pirfenidone, piroxicam, piroxicam cinnamate, piroxicam olamine, pirprofen, prednazate, prifelone, prodolic acid, proquazone, proxazole, proxazole citrate, rimexolone, romazarit, salcolex, salnacedin, salsalate, sanguinarium chloride, seclazone, sermetacin, sudoxicam, sulindac, suprofen, talmetacin, talniflumate, talosalate, tebufelone, tenidap, tenidap sodium, tenoxicam, tesicam, tesimide, tetrydamine, tiopinac, tixocortol pivalate, tolmetin, tolmetin sodium, triclonide, triflumidate, zidometacin, zomepirac sodium, aspirin (acetylsalicylic acid), salicylic acid, corticosteroids, glucocorticoids, tacrolimus and pimecrolimus.

In addition to the specific embodiments claimed below, the disclosed subject matter is also directed to other embodiments having any other possible combination of the features herein. As such, the particular features presented in the claims and disclosed above can be combined with each other in other manners within the scope of the disclosed subject matter such that the disclosed subject matter should be recognized as also specifically directed to other embodiments having any other possible combinations. Thus, the foregoing description of specific embodiments of the disclosed subject matter has been presented for purposes of illustration and description. It is not intended to be exhaustive or to limit the disclosed subject matter to those embodiments disclosed.

It will be apparent to those skilled in the art that various modifications and variations can be made in the method and system of the disclosed subject matter without departing from the spirit or scope of the disclosed subject matter. Thus, it is intended that the disclosed subject matter include modifications and variations that are within the scope of the appended claims and their equivalents.

The following examples are presented in order to more fully illustrate certain embodiments of the invention. These examples in no way, however, should be construed as limiting the broad scope of the invention. One skilled in the art can readily devise many variations and modifications of the principles disclosed herein without departing from the scope of the invention.

EXAMPLES

The present invention will be further understood by the examples set forth below. The following examples are merely illustrative of the present invention and should not be considered as limiting the scope of the invention in any way.

Example 1

Effect of Acetone Vapor Exposure on a Coated Glass Slide

In this example, a coating was applied to a glass slide and the drug coated slide was then exposed to acetone vapor to reduce porosity and increase opaqueness in the coating.

METHODS/MATERIALS: The drug solution consists of a 2:1:0.4 w/w ratio of Zotarolimus:PVP:Glycerol formulated in 85:15 Acetone:Ethanol as a 5 wt % Zotarolimus concentration. The acetone used was ACS Reagent>99.5%, Sigma-Aldrich, PIN 673781-1L.

Using a 5 mL pipette, one to three drops of the drug solution were deposited onto a 90×50 mm glass slide to form three individual droplets of coating. The appearance of each droplet changed into the final appearance within 15 seconds. The glass slide was allowed to dry under ambient room temperature and uncontrolled humidity for one hour and did not change in appearance. After solidification, the slide was then positioned inside an 8×10 mm Ziploc recloseable bag and sealed for 10 minutes under ambient conditions. A 90×50 mm glass beaker was filled with 150 mL of acetone and placed within the Ziplock recloseable bag. The bag was sealed and placed inside of a fume hood for five minutes at ambient room temperature. The coated glass slides were imaged using a Leica optical microscope.

Figures 3A, 3B:
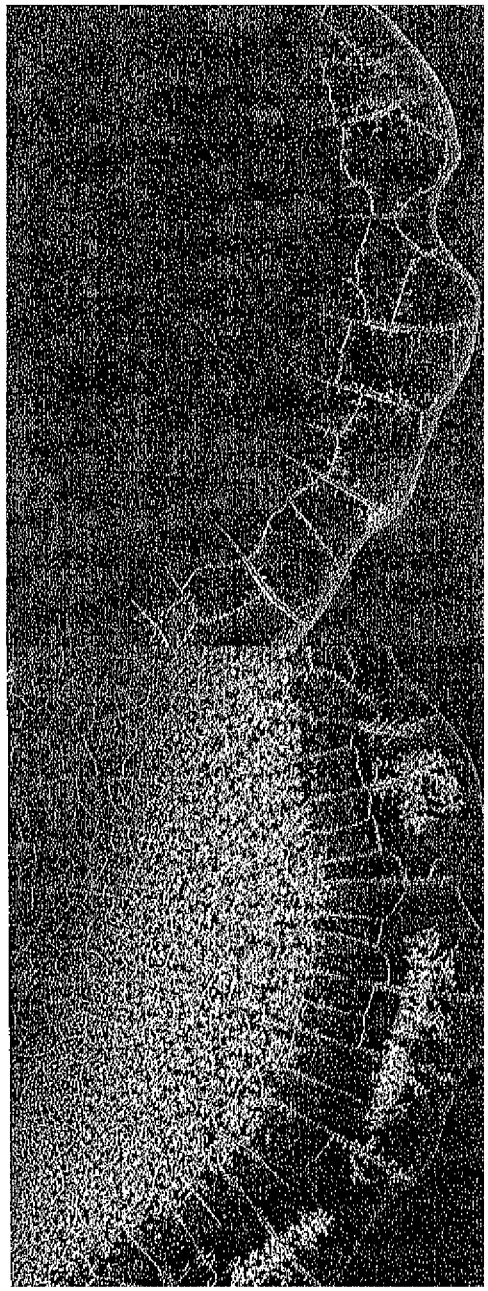

RESULTS: FIGS. 1A, 2A, and 3A show the glass slide at 30×, 150×, and 200× magnification prior to exposure to the acetone vapor. FIGS. 1B, 2B, and 3B show the glass slide at 30×, 150×, and 200× magnification after exposure.

DISCUSSION: Prior to exposure, fractal crystal growth is observed within the grain of the coating, producing an opaque appearance. After exposure, the grains of the coating became transparent. Furthermore, the outer most boundary of the coating kept the same configuration between the untreated and treated coating, indicating that the vapor allowed internal transformations without causing the system to enter into a liquid state. The ability to maintain defined edges is beneficial in drug coated balloons where the working length is controlled and coating flow to the tapered ends is undesirable.

Example 2

Effect of Acetone Vapor Exposure on a Drug Coated Balloon

In this example, drug coated balloons were exposed to acetone vapor to smooth out the coating morphologies.

METHODS/MATERIALS: The same drug solution, acetone, and system comprising a Ziploc recloseable bag in a fume hood from Example 1 were used. Two Agiltrac 0.035 balloons were processed with IPA sonication for 1 minute, dried off with nitrogen air for 5 minutes, and allowed to reach an equilibrated state for 30 minutes. The systems were then coated using the standard direct fluid application method wherein a coating was applied to a balloon external surface during its rotation/linear traversing and nitrogen gas was drying the balloon immediately for ten seconds after the coating was deposited.

The first balloon had a coating of 88 $\mu g/cm^2$ and the second balloon had a coating of 400 $\mu g/cm^2$. The balloons were kept at a pressure state open to air and remained in ambient temperature and uncontrolled humidity conditions throughout this experiment. The drug coated balloons were exposed to 150 mL of acetone for 7.5 minutes, which was the time it took to observe the coating appearance change from translucent to transparent. They were imaged prior to and after vapor exposure using a Leica optical microscope.

RESULTS: FIG. 4A shows the 88 $\mu g/cm^2$ coated balloon at 40× magnification prior to vapor exposure. FIG. 4B shows the 88 $\mu g/cm^2$ coated balloon at 40× magnification after vapor exposure. FIG. 5A shows the 400 $\mu g/cm^2$ coated balloon at 40× magnification prior to vapor exposure. FIG. 5B shows the 400 $\mu g/cm^2$ coated balloon at 40× magnification after vapor exposure.

DISCUSSION: FIG. 4A shows that the unexposed coating of the coated balloon exhibits a porous morphology consisting of a small stucco pattern. FIG. 4B displays that after vapor exposure the small stucco pattern is nearly diminished leaving only fine dislocations and some minor indentations of the same stucco pattern. In FIG. 5A, the left coated balloon has a spongy, porous morphology consisting of a large stucco pattern. As seen in FIG. 5B, after exposure to acetone vapors the large stucco pattern nearly diminished, leaving only fine dislocations and some indentations of the same large stucco pattern. These changes in morphologies observed with balloon coatings is consistent with the observations made on the glass slide coatings.

Example 3

Scratch Test of a Drug Coated Balloon

A scratch test was performed on a coated balloon prior to and after vapor exposure to demonstrate the increased scratch resistance of the coating after exposure.

METHODS/MATERIALS: An Agiltrac 0.035 balloon with a coating of 400 μg/cm$^2$ was prepared according to the method in Example 2. A standard scratch test was performed on the balloon coating using the edge of a flared PTFE sheath to visually observe any deformation of the coating. The balloon was then treated with vapor exposure according to the method in Example 2.

RESULTS: Prior to vapor exposure, the coating was easily deformed. After exposure, the coating did not deform.

DISCUSSION: The surface appears to increase in hardness following the vapor exposure as it is more resistant to localized deformation.

Example 4

Effect of Vapor Exposure on Surface Friction of Drug Coated Balloons

The pull force required to remove a sheath from a drug coated balloon was measured for unexposed and vapor exposed balloons to demonstrate that exposure reduces the surface friction of a drug coated balloon.

METHODS/MATERIALS: This experiment uses the same vapor exposure method as in Experiment 1. Six Fox SV balloons were attained from a build known from previous experiments to have a high frictional surface force due to the increase in coating striations and a large drug dose of 600 μg/cm$^2$.

These balloons were coated with a 2:1:0.4 w/w PVP: Zotarolimus:Glycerol (7% Zotarolimus w/w) solution. The balloons were coated by the same method used in Example 2. The first control set of three coated balloon systems were folded and sheathed with a 0.079" FEP sheath. The second set of three coated balloon systems were exposed to 150 mL of acetone vapor for 7.5 minutes. Following vapor treatment and drying time under ambient temperature and uncontrolled humidity for thirty minutes, the coated balloon was folded and sheathed with a 0.079" FEP sheath. The sheath pull forces of the two sets were then tested using an Instron IX Series tester. The sheath pull force is calculated as the amount of force needed to remove the sheath from the drug coated balloon system.

Figure 6:
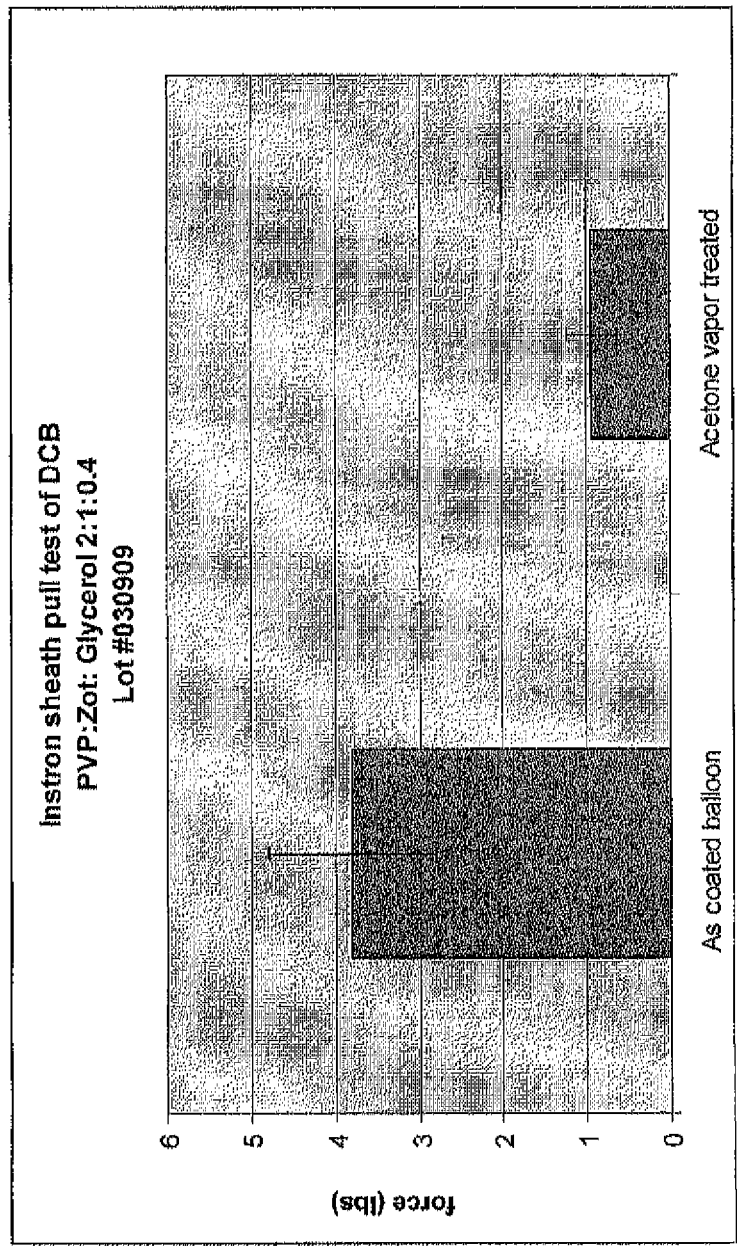
FIG. 6 is a bar graph illustrating the results from a comparative study of sheath pull force (lbs) for drug coated balloons as described in Example 4, wherein the graph shows the average pull force (y-axis) for three balloons prior to exposure and three balloons after exposure to acetone vapor (x-axis).
Figure 7A:
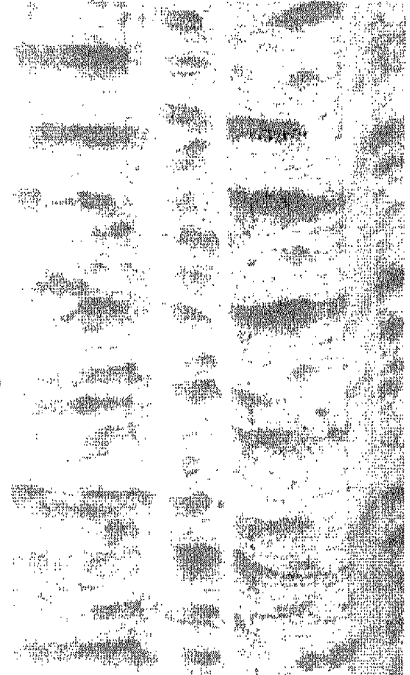
Figure 7B:
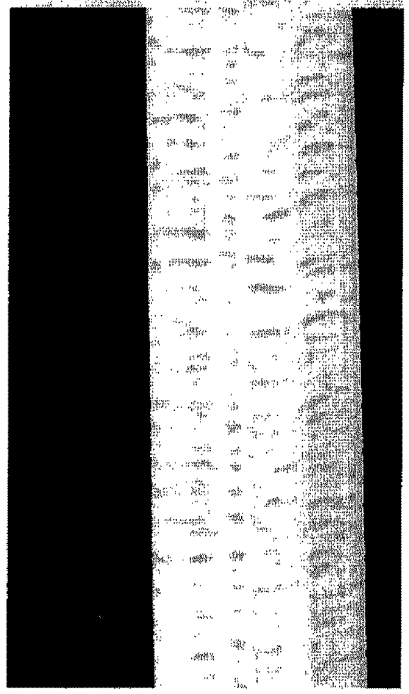
Figure 7C:
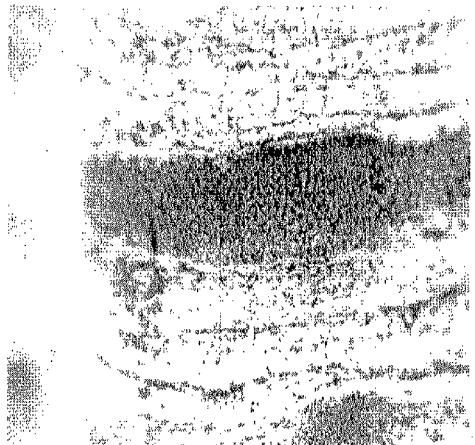
Figure 7D:

RESULTS: The bar graph from FIG. 6 shows that the average force to remove the untreated set (n=3) was 3.80 lbs of force with a standard deviation of 0.937. The bar graph also shows the treated set (n=3) needed 0.995 lbs of force with a standard deviation of 0.305.

DISCUSSION: This result indicates that a vapor treatment method can also reduce the frictional force between the coating surface and protective sheath. In this example, this would improve the ease of use for this device as it would require less force for the user to remove the balloon sheath. In addition, lower frictional forces when the sheath is removed from a drug coated balloon system typically correlate with maximized drug content recovery. In one study, 18 balloons were coated with 300 μg/cm$^2$ Zotarolimus/PVP/Glycerol 2/1/0.4 w/w. The 18 balloon systems were divided into three groups and received various plasma treatments. All systems were processed with IPA sonication for 1 minute, dried off with nitrogen air for 5 minutes, allowed to reach an equilibrated state for 30 minutes and coated using the standard direct fluid application method wherein a coating was applied to a balloon external surface during its rotation/linear traversing and nitrogen gas was drying the balloon immediately for ten seconds after coating was deposited. The drug recovery and sheath adhesion test results were as followed: Group 1: Drug Recovery—101.56%, SD 3.1%; Sheath Adhesion—1.361 lbs, SD 0.337 lbs. Group 2: Drug Recovery—99.40%, SD 2.4%; Sheath Adhesion—1.904 lbs, SD 0.394 lbs. Group 3: Drug Recovery—96.60%, SD 2.5%; Sheath Adhesion—2.199 lbs, SD 0.385 lbs. The results demonstrated how the trending of a lower frictional results, correlate with upper drug content recovery.

Example 5

Effect of Water Vapor Exposure on Coated Balloons

In this experiment, drug coated balloons were exposed to water vapor at high temperature to smooth out the coating morphologies.

METHODS/MATERIALS: A Fox SV balloon was coated with 300 μg/cm$^2$ Zotarolimus/PVP/Glycerol 2/1/0.4 w/w by direct vapor application. The balloon was coated by the same method used in Example 2. The coating was uniform across the working length of the balloon (distal to middle to proximal). The drug coated balloon was suspended in convention oven set to 60° C. with a beaker of water for 18 hours.

RESULTS: FIGS. 7A-D depict the coated balloon at 50×, 200×, 200×, and 400× magnification, respectively, prior to water vapor exposure. FIGS. 8A-D depict the coated balloon at 50×, 200×, 200×, and 400× magnification, respectively, after water vapor exposure.

DISCUSSION: Prior to water vapor exposure the coating exhibits striations. After exposure the coating has fewer striations and a smoother morphology.

The disclosed subject matter can be embodied in other specific forms without departing from its spirit or essential characteristics. The described embodiments are to be considered in all respects only as illustrative and not restrictive. Thus, it is intended that the disclosed subject matter include modifications and variations that are within the scope of the appended claims and their equivalents. All references recited herein are incorporated herein in their entirety by specific reference.

\* \* \*

All patents, patent applications, publications, product descriptions and protocols, cited in this specification are hereby incorporated by reference in their entirety. In case of a conflict in terminology, the present disclosure controls.

While it will be apparent that the invention herein described is well calculated to achieve the benefits and advantages set forth above, the present invention is not to be limited in scope by the specific embodiments described herein. It will be appreciated that the invention is susceptible to modification, variation and change without departing from the spirit thereof.

What is claimed is:

1. A method of modifying coating morphology of a balloon catheter, the method comprising, in the following sequence:
applying a liquid coating including a therapeutic agent and an excipient to a surface of a balloon;
curing the liquid coating having the initial coating morphology on the surface to form a coated balloon, wherein curing includes drying the liquid coating to a solid state having an initial coating morphology with cracks and fractures on the surface of the coating;
altering the initial coating morphology by exposing the coated balloon to only a solvent vapor to provide the coating with an altered coating morphology; and
drying the coating having the altered coating morphology on the coated balloon, wherein the altered coating morphology has less crazing, fewer cracks and fractures, or reduced porosity in the coating as compared to the initial coating morphology.

2. The method of claim 1, wherein drying occurs in a closed or semi-enclosed system, simultaneously with exposure to the solvent vapor, or by applying directed vapor in line.

3. The method of claim 2, wherein the applying directed vapor in line occurs via a nozzle located between about 1 mm and about 200 mm from the coated balloon.

4. The method of claim 2, wherein the directed vapor is at a pressure between about 10 torr and about 1520 torr.

5. The method of claim 1, wherein drying the coating with the altered coating morphology on the coated balloon removes residual solvent from the coating.

6. The method of claim 1, wherein the coating is applied by spraying, syringe coating, direct fluid application, spin coating, vapor deposition, roll coating, micro-droplet coating, drip coating, dip coating, electrospinning, electrostatic coating, direct vapor application or a combination thereof.

7. The method of claim 1, wherein the coating comprises a polymeric coating, elastomeric coating, hydrophilic coating, hydrophobic coating, drug coating, drug excipient coating, biologic agent coating, protein coating, silicone coating, radiopaque coating, or a combination thereof.

8. The method of claim 1, wherein the therapeutic agent includes an anti-proliferative agent, a pro-proliferative agent, anti-inflammatory agent, anti-thrombotic agent, thrombolytic agent, anticoagulant agent, antiplatelet agent, anti-metabolite agent, anti-neoplastic agent, anti-mitotic agent, anti-fibrin agent, cytostatic agent, cytoprotective agent, ACE inhibiting agent, cardioprotective agent, antibiotic agent, anti-allergic agent, antioxidant agent, smooth muscle cell migration inhibiting agent, anti-smooth muscle cell proliferation agent, reendothelialization agent, plaque deposition inhibiting agent, restenosis-limiting agent, or a combination thereof.

9. The method of claim 1, wherein the therapeutic agent includes everolimus, zotarolimus, rapamycin, biolimus, myolimus, novolimus, deforolimus, temsirolimus, paclitaxel, protaxel, analogs and derivatives thereof, or a combination thereof.

10. The method of claim 1, wherein the vapor has a vapor pressure between about 0.5 torr and about 420 torr at 20° C.

11. The method of claim 1, wherein the vapor is volatile.

12. The method of claim 11, wherein the volatile vapor has a boiling point at ambient pressure in the range of about 25° C. to about 185° C.

13. The method of claim 11, wherein the volatile vapor comprises acetone, methanol, ethanol, 2-propanol, 1-propanol, linear alcohols, methane, ethane, propane, butane, pentane hexane, cyclohexane, heptane, methyl iso-butyl ketone, methyl ethyl ketone, dimethylsulfoxide, dimethylacetamide, dimethylformamide, formamide, methyl acetate, ethyl acetate, propyl acetate, isopropyl acetate, n-butyl acetate, dimethyl ether, diethyl ether, dipropyl ether, N-methylpyrrolidone, dichloromethane, chloroform, difluoromethane, fluoroform, freons, benzene, toluene, xylene, blends thereof, and combinations thereof.

14. The method of claim 13, wherein the solvent is acetone.

15. The method of claim 1, wherein the coating having the initial coating morphology has a glass transition temperature, and further wherein exposing the coated balloon to the solvent vapor comprises maintaining a temperature above the glass transition temperature of the coating having the initial coating morphology on the coated balloon.

16. The method of claim 1, wherein the coating having the initial coating morphology has a glass transition temperature, and further wherein exposing the coated balloon to the solvent vapor causes the glass transition temperature of the coating having the initial coating morphology to drop so that it is below the temperature of the solvent vapor treatment.

17. The method of claim 1, wherein exposing the coated balloon to the solvent vapor comprises exposing the coated balloon to ambient temperature.

18. The method of claim 1, wherein exposing the coated balloon to the solvent vapor comprises maintaining a pressure that ranges from about 10 torr to about 1520 torr.

19. The method of claim 1, wherein exposing the coated balloon to the solvent vapor comprises maintaining a pressure that ranges from about 50 torr to about 760 torr.

20. The method of claim 1, further comprising maintaining the coated balloon stationary while exposing the coated balloon to the solvent vapor.

21. The method of claim 1, further comprising rotating the balloon while exposing the coated balloon to the solvent vapor.

22. The method of claim 21, wherein the coated balloon is rotated manually or automatically via a rotating motor at set speeds greater than zero RPM.

23. The method of claim 21, wherein the coated balloon is rotated at set speeds between about 5 RPM and about 700 RPM.

24. The method of claim 21, wherein the is attached to a stage and the stage is linearly translated at a speed between about 0.1 mm/sec to about 5 mm/sec.

25. The method of claim 1, wherein exposing the coated balloon to the solvent vapor includes placing at least a portion of the coated balloon in a closed or semi-enclosed system.

26. The method of claim 25, wherein the closed system is an enclosed chamber.

27. The method of claim 1, wherein exposing the coated balloon to the solvent vapor comprises applying directed solvent vapor in line.

28. The method of claim 27, wherein the applying directed solvent vapor in line occurs via a nozzle located between about 1 mm and about 200 mm from the coated balloon.

29. The method of claim 27, wherein the directed solvent vapor is at a pressure between about 10 torr and about 1520 torr.

30. The method of claim 1, wherein exposing the coated balloon to the solvent vapor causes internal transformation within the coating without the coating entering a liquid state.

31. The method of claim 1, wherein exposing the coated balloon to the solvent vapor causes the coating to have reduced crystallinity and become amorphous or semi-amorphous.

32. The method of claim 1, wherein exposing the coated balloon to the solvent vapor causes the coating to flow such that the morphology of the coating is altered.

33. The method of claim 1, wherein the coated balloon is exposed to the solvent vapor for a length of time between about 5 minutes and about 18 hours.

34. The method of claim 1, wherein the coated balloon is exposed to the solvent vapor for a length of time between about 5 minutes and about 7 hours.

35. The method of claim 1, wherein the altered coating morphology reduces frictional force between the coating surface and a protective sheath as compared to a similar balloon having a coating with an unaltered coating morphology.

36. The method of claim 1, wherein altering the initial coating morphology occurs without the cured coating entering a liquid state.

* * * * *